United States Patent [19]
Wainer et al.

[11] Patent Number: 5,871,013
[45] Date of Patent: Feb. 16, 1999

[54] REGISTRATION OF NUCLEAR MEDICINE IMAGES

[75] Inventors: Naor Wainer; Shoulamit Cohen Shwartz, both of Haifa, Israel

[73] Assignee: Elscint Ltd., Haifa, Israel

[21] Appl. No.: 571,429

[22] Filed: Dec. 13, 1995

Related U.S. Application Data

[62] Division of Ser. No. 454,871, May 31, 1995, abandoned.

[51] Int. Cl.$^6$ ...................................................... A61B 6/00
[52] U.S. Cl. ...................... 128/653.1; 128/659; 128/696; 128/716; 250/363.04
[58] Field of Search ................................ 128/653.1, 659, 128/696, 708, 716, 721; 250/363.04

[56] References Cited

U.S. PATENT DOCUMENTS

| 4,617,938 | 10/1986 | Shimoni et al. | 128/708 |
| 5,099,846 | 3/1992 | Hardy | 128/653.1 |
| 5,210,412 | 5/1993 | Gullberg et al. | 250/363.04 |
| 5,210,421 | 5/1993 | Gullberg et al. | 250/363.04 |
| 5,672,877 | 9/1997 | Liebig et al. | 250/363.04 |

OTHER PUBLICATIONS

Pellizari et al., C.A., "Accurate Three-Dimensional Registration of CT, PET, and/or MR Images on the Brain," Journal of Computer Assisted Tomography, vol. 13, pp. 20–26, 1989.
Woods et al., R.P. "MRI–PET Registration with Automated Algorithm," Journal of Computer Assisted Tomography, vol. 17, pp. 536–546, 1993.
Alpert et al., N.M., "The Principal Axes Transformation—A Method for Image Registration," The Journal of Nuclear Medicine, vol. 31, pp. 1717–1722, 1990.
Thirion, Jean–Phillipe, :"The Extremal Mesh and the Understanding of 3D Surfaces," Research Report No. 2149, Institut National de Recherche en Informatique et en Automatique (INRIA), Dec. 1993.
Thirion, Jean–Phillips, "New Feature Points Based on Geometrical Invariants for 3D Image Registration," Research Report No. 1901, Institut National de Recherche en Informatique et en Automatique (INRIA), May 1993.

Primary Examiner—Ruth S. Smith
Attorney, Agent, or Firm—Fenster & Company

[57] ABSTRACT

A method of registering a plurality of functional images using both structural images and gating.

11 Claims, 4 Drawing Sheets

REGISTRATION OF NUCLEAR MEDICINE IMAGES

This application is a divisional application of U.S. application Ser. No. 08/454,871, filed on May 31, 1995, abandoned and is related to the divisional application Ser. No. 08/572,799, filed currently herewith and which is also a division of the same application.

FIELD OF THE INVENTION

The present invention relates to the art of diagnostic imaging. In particular, the invention relates to nuclear imaging systems incorporating simultaneous transmission and emission tomography.

BACKGROUND OF THE INVENTION

SPECT (Single Photon Emission Computerized Tomography) is used to study the three dimensional distribution of a radionuclide in a patient. Typically one or more radiopharmaceuticals are ingested or are injected into the patient. When radiopharmaceuticals are injected it is usually into the patient's blood stream, to image the cardio-vascular system or to image specific organs which absorb the injected radiopharmaceuticals. One or more gamma or scintillation detectors are positioned near the patient to record emitted radiation.

SPECT images are generally produced by:

(a) rotating the detector(s) around the patient in order to record emissions from a plurality of directions; and (b) transforming the recorded emissions, using methods well known in the art, into a tomographical multi-slice image, a three dimensional image or some other representation of the distribution of the radiopharmaceutical injected into the patient's body.

One problem with SPECT is that the tissues surrounding the organs being imaged attenuate and scatter the radiation emitted by the radiopharmaceutical, distorting the resulting SPECT images. to solve this problem, a SPTCT (Single Photon Transmission Computerized Tomography) image of the region being imaged, is acquired, simultaneously with the SPECT image. The SPECT image provides information regarding the attenuation and scattering characteristics of the region being imaged, so that the multi-view emission data can be corrected.

In order to acquire the simultaneous SPTCT image, a source of radiation is placed opposite the patient's body from the detector(s) and rotated with the detector(s). Preferably, but not necessarily, the energy of the SPTCT source is different from that of the radiopharmaceutical so that the detector is able to easily differentiate the two radiations.

Since the emission image is acquired at the same time as the transmission image, and the relative geometry of the SPTCT and SPECT systems are known, the images are easily registered to one another.

The diagnostic method that uses SPECT and SPTCT simultaneously is known as STET (Simultaneous Transmission and Emission Tomography). This method is described in further detail in U.S. Pat. No. 5,210,421, the disclosure of which is incorporated herein by reference.

One aspect of the present invention relates to the use of STET imaging techniques for functional imaging. In this use the resultant STET image shows the metabolic activity of body tissue, since dead or damaged body tissue absorbs the radiopharmaceutical at a different rate (or not at all) from healthy tissue. When used in this manner, the STET image shows the functional activity of the body tissue, not its structural detail.

However, STET images have two drawbacks. First, as indicated above, the STET image does not show much structural detail; therefore it is difficult to pinpoint where the imaged function is occurring in the patient's body. Many diagnostic imaging methods in modalities other than nuclear medicine, reveal almost exclusively structure and not function, therefore, it is hard to compare STET images with other types of diagnostic images. Second, a common methodology especially in cardiac examination, is to acquire a STET image shortly after injection of the radiopharmaceutical and to acquire another STET image of the same region after a certain period of time. By comparing these two (or more) images it is possible to learn still more about the function of the tissue studied, such as the speed at which different portions of tissue absorb and metabolize the radiopharmaceutical. However, if the two STET images are too different, it is not possible to closely compare them because the operator cannot match the different parts of the images to each other.

SUMMARY OF THE INVENTION

The present invention contemplates a method for registering STET images and other functional images to images of other modalities, and for matching two STET images taken at different times of the same body region, thereby solving the above mentioned problems.

In accordance with one preferred embodiment of the present invention a method for matching two STET images acquired at different times uses the SPTCT data in order to identify structure in the patient's body. When two STET images are to be compared, the two respective SPTCT images are registered, preferably, using a correlation method or another known image matching method. Since the STET is registered to its SPTCT image, registering the two SPTCT images automatically registers the two STET images.

In accordance with another preferred embodiment of the present invention, a method for registering a STET image and a structural diagnostic image (such as an MRI, ultrasound or X-ray CT image) uses the SPTCT data in order to identify structure in the patient's body. When the STET image is to be registered to the structural diagnostic image, the structural SPTCT image and the structural diagnostic image are registered. This registration is preferably accomplished through the choosing and comparing of prominent body structures, such as the skeleton, organs or body outlines. Once this matching is accomplished, a mapping between the images can be defined, based on the mapping between the prominent body structures chosen. This mapping is used to transform one image so that it can be superimposed over the other image.

Alternatively, prominent body markings on the SPTCT image are saved as fiduciary marks with the STET image. These marks are used to match the STET image to another structural image.

In accordance with yet another preferred embodiment of the present invention, a method for registering a first SPECT image to a structural diagnostic image uses a second SPECT image to serve as a structural image. Two SPECT images are acquired of the studied region, the first image is acquired using a first radiopharmaceutical, which is selected so that the resultant SPECT image shows the desired function. The second SPECT image is acquired using a second radiopharmaceutical, which is selected so that the resultant image shows some structure such, as outlines of organs which can be used to register the second SPECT image to another structural image. Alternatively, parameters other than the radiopharmaceutical are varied in order to generate the different SPECT images.

Matching between the second SPECT image and the structural diagnostic image is accomplished through the choosing and comparing of prominent body structure shown in both images. Preferably, the two SPECT images are acquired simultaneously using a dual isotope gamma camera, so that they are automatically registered.

A mapping between the first SPECT image and the structural diagnostic image is then created based on the inherent registration between the two SPECT images and the matching between the second SPECT image and the structural diagnostic image. It should be noted that this preferred embodiment does not require a STET device (although one can be used), a SPECT device is sufficient.

In a simple situation, the size and shape of the image is not affected and only transmission and/or rotation is required. Where scaling is required, one of the images is scaled in accordance with the correlation of a plurality of chosen structural features or of the images as a whole. In one embodiment of the invention, warping and other complex corrections can be applied to improve the match between the images.

The term "structural image" as used herein means an image that is used to compare structures. The term "functional image" as used herein means a functional image that is not used to determine registration. As can be appreciated, functional images may show structure and a substantial amount of structure in structural images may be caused by functionality.

Preferably for many types of studies, the acquisition of SPECT, SPTCT and STET images is synchronized to the cardiac rhythm, the respiratory rhythm or other body motions by gating. In such gated images data acquired during the imaging process is binned (or windowed) according to a gating signal derived from the body rhythm.

Thus, in a preferred embodiment of the invention, image acquisition is gated to body rhythms and motions. Preferably, the structural images are also synchronized in the same manner. For example, gated CT images are used as structural images instead of regular CT images when the STET images are gated. An advantage of combining STET imaging with gating is the ability to correct binned data for patient motion during data acquisition by realignment based on the registration of the images. This corrects for smearing otherwise produced by patient motion. Additionally, data from separate bins is more easily combined.

Another advantage is the ability to correct organ motion caused by the gated rhythm by applying a geometric transformation to data acquired based on the phase of the gated rhythm. Yet another advantage is the ability to register transmission images to emission images even when they are not acquired simultaneously. A transmission image of a patient which is gated to body rhythms can be automatically registered to its corresponding gated emission image, since most of the misalignment between the two images is caused by body rhythms which are, in general repetitive.

DETAILED DESCRIPTION OF THE PREFERRED EMBODIMENT

The present invention does not require the use of any specific STET device, and for most devices the invention can be practiced by changes and/or additions in image processing and registration.

In addition, it is possible to use the present invention with NON-STET devices, provided that the SPECT and SPTCT images can be registered to each other.

Figure 1:
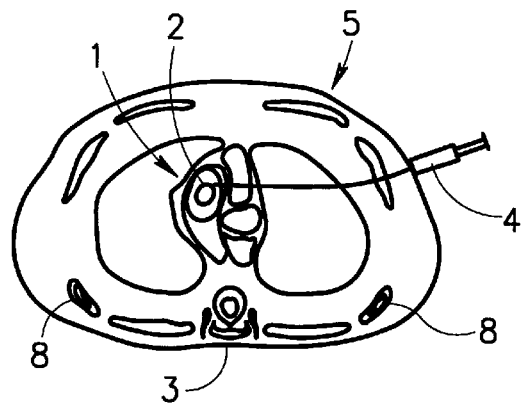
FIG. 1 is a partial simplified schematic view of a slice of the human body in the chest region showing the heart ribs and a portion of functioning heart tissue.

FIG. 1 in U.S. Pat. No. 5,210,421 shows a typical STET camera assembly which is used for acquiring STET images.

The process for acquiring these images typically includes:
(a) placing a patient on a couch, so that the part to be studied will be in an examination area;
(b) injecting a radiopharmaceutical into the patient;
(c) acquiring pairs of SPTCT and SPECT images using one or more detectors;
(d) rotating the detector(s) around the examination area, in order to acquire a plurality of image pairs;
(e) transforming the plurality of image pairs into a multi-slice tomographical STET image a three dimensional STET image or another representation of STET data, the SPTCT images being employed to correct the attenuation and scattering artifacts in the SPECT images to produce the STET images.
(f) optionally after an attending physician examines this image, the patient is sent to rest and/or exercise and/or reinjection;
(g) after a period of rest or exercise the image acquisition process is typically repeated, with the patient placed in as nearly as possible the same position as during the previous study, so as to facilitate comparing the new images with the old ones.

Preferably for many types of studies, the acquisition of SPECT, SPTCT and STET images is synchronized to the cardiac rhythm, the respiratory rhythm or other body motions by gating. In such gated images data acquired during the imaging process is binned (or windowed) according to a gating signal derived from the body rhythm.

The following discussion refers to a section of the patient's body being imaged shown in FIG. 1. FIG. 1 is simplified to include only a heart 1 including a functionally active area 2 of the heart, ribs 8 and a backbone 3. In order to simplify the discussion, only one slice is shown even though the STET image is three dimensional. Application of the invention to three dimensions and choosing the correct slices is described below.

Figure 2A:
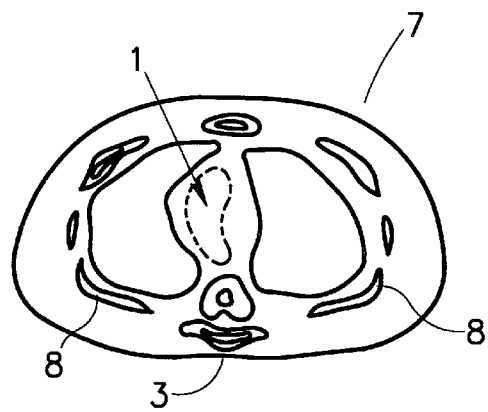
FIG. 2A is a simplified schematic of a SPTCT scan of the body slice from FIG. 1.
Figure 2B:
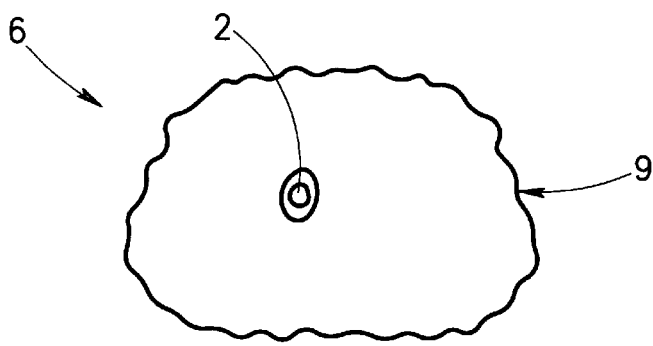
FIG. 2B is a simplified schematic of a STET image of the body slice shown in FIG. 1.
Figure 2C:
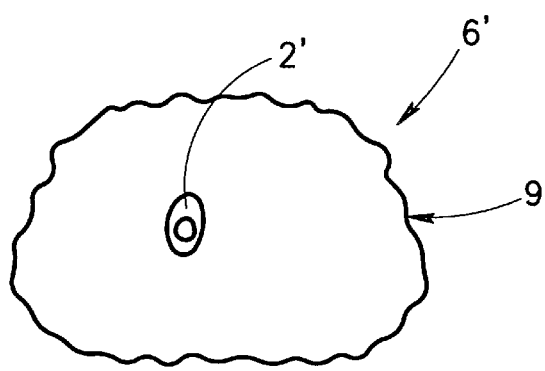
FIG. 2C is a simplified schematic of a STET image of the body slice shown in FIG. 1, acquired at a different time from FIG. 2B.

FIG. 2B shows a STET image 6 of the body slice shown in FIG. 1, such as would be acquired in a heart study. In such studies, most of the radiopharmaceutical is concentrated in the blood or in soft tissues and specific organs such as the heart and liver, so that the acquired STET image 6 shows mostly portions of target organs and a fuzzy outline 9 of the patient's body. FIG. 2C shows a later STET image 6' of the same region in the same patient. With the passage of time, the radiopharmaceutical is absorbed and metabolized by the body tissues, and the STET image changes, as can be seen by comparing image 6 with image 6'. In FIG. 2C a functionally active area 2' is imaged which is larger than area 2.

FIG. 2B and FIG. 2C are STET images 6 and 6' of the region shown in FIG. 1. The images 6 and 6' show functionally active areas 2 and 2' respectively but not bones such as the ribs 8 or even the non-active areas of heart 1. FIG. 2A shows a very simplified SPTCT image 7 which is a structural image much, like a standard X-ray CT, except for poorer resolution and lower organ definition ability. The SPTCT image 7 shows heart 1, ribs 8 and even backbone 3, but does not specifically differentiate the functionally active areas of the heart.

In the later STET image 6', of FIG. 2C, there are significant changes from the earlier STET image 6, of FIG. 2B making it difficult, if not impossible to match correctly functioning area 2 in image 6 with functioning area 2' in image 6'. In addition, it is difficult to identify correctly the structural areas which are functioning as revealed by the radiopharmaceutical.

A second SPTCT image is acquired simultaneously with image 6'. The SPTCT images acquired with images 6 and 6' are very similar, since the patient's body structure does not change much between the images, and the continuing of the radiopharmaceutical which plays a crucial part in images 6 and 6' does not play a part in SPTCT imaging. Two types of differences between the two SPTCT images are caused by:

(a) changes due to patient movement caused, for example, by breathing; and
(b) changes due to different placement of the patient on the examination table.

Since the respective emission and transmission images are acquired with the same known system geometry, the mapping of the emission image to its respective transmission image is also known, so the two respective images can be considered registered to each other. The following discussion assumes that any necessary registration between the two respective images has been performed.

A preferred embodiment of the invention uses the following process in order to transform a SPTCT structural image, which has an associated registered STET image, so that it is registered to a structural image:

(a) marking prominent body structure in the two structural images;
(b) correlating the prominent structures between the structural images;
(c) determining a transformation between the two structural images, based on the correlation between the structures; and
(d) transforming the SPTCT image in accordance with the transformation found in (c).

The transformation will have a degree of complexity appropriate to the image being aligned, and may include:
(i) simple alignment of the images;
(ii) scaling of one of the images; and
(iii) warping one of the images.

The functional STET image associated with the SPTCT image is transformed using the same transformation as that used for the SPTCT image.

In a preferred embodiment of the invention, registering of two STET images 6 and 6' is achieved by registering the two respective associated SPTCT images using the above described method. The registration of STET images 6 and 6' follows automatically.

Figure 3:
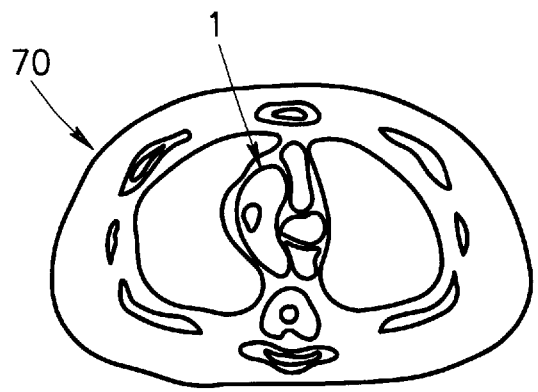
FIG. 3 is a simplified schematic X-ray CT image of the body slice shown in FIG. 1.

In an additional preferred embodiment of the invention a STET image 6 is to be registered to a structural image such as a X-ray CT image, a MRI image or an ultrasound image. FIG. 3 shows a CT image 70, such as is to be registered to STET image 6. The registration is performed by using the above described process to register SPTCT image 7, that is associated with STET image 6, to CT image 70. The registration of STET image 6 to CT image 70 follows automatically, using the same transformation used to register the two structural images.

In yet another preferred embodiment of the invention, SPECT image is registered to a structural image, such as an X-ray CT image, using a second SPECT image as a structural image instead of using a SPTCT image. A SPECT device is used to simultaneously acquire two images, with one image showing enough structure to be used as a structural image. The two images are acquired using a dual isotope gamma camera and a different radiopharmaceutical for each image. Since the functional and the structural SPECT images are automatically registered, registering the structural SPECT image with the X-ray CT image or other structural automatically registers the functional SPECT image with the X-ray CT image or other structural image. Accordingly, the registration between the structural SPECT image and the structural image is performed by using the above described registration process. The registration of the functional SPECT image to the structural image follows automatically, using the same transformation used to register the two structural images.

For example, to detect and locate malignant liver lesions, two SPECT images and one CT image are acquired of the liver. A first SPECT image, which is acquired using FDG, highlights only malignant tumors and shows little body structure. A second SPECT image, acquired simultaneously using intravenously injected Tc99 m colloid, clearly shows the anatomic boundaries of the liver and lesions. A CT image of the liver and surrounding tissue also clearly shows the anatomic boundaries of the liver and lesions. Therefore, the CT image (the structural image) is registered to the second SPECT image (the structural SPECT image) using the registration process described herein. Consequently, the first SPECT image is registered to the CT image (because the two SPECT images are acquired simultaneously and ,therefore, automatically registered to each other) so that the malignant lesions can be pointed out on the CT image.

Typically a three dimensional image is acquired and processed as a series of two dimensional slices. In order to properly register slices of three dimensional images, as described above, slice pairs that have the same location along the patient's longitudinal (Z) axis must be chosen.

In the case of matching two STET images corresponding slices from the two SPTCT images, must be chosen. Two preferred methods for matching slices are:
(i) The operator chooses the appropriate slices based on his/her understanding of the images and his/her knowledge of human anatomy; and
(ii) since the image modality is the same for both SPTCT images, a computer can search for the closest matching slice pair using a correlation algorithms.

Once the closest matching slices are found, the process continues as described above. Alternatively, using image matching techniques known in the art of image processing, the two SPTCT images can be matched in the axial direction with a precision higher than the width of a slice. Since the STET image is a true three dimensional image, one of the two images can be "resliced", so that the image slices of one STET image are exactly aligned to the slices of the other STET image.

In the case of registering a STET image to an X-ray CT image, the preferred way to find the correct matching CT and SPTCT slices is to have the physician choose the slice pair, based on his understanding of the images and his knowledge of human anatomy. Once the closest matching slices are found the STET image can be re-sliced so that the STET image slices fall on boundaries of the CT slices. For images derived from different modalities, the Z scale may be different. A slice scale factor may be derived based on matching a plurality of structural features in different slices.

In an additional preferred embodiment of the invention, steps (a) and (b) of the registration process are replaced by a single step of correlating the two images as a whole. Additionally three dimensional images may also be correlated as wholes, without first slicing them and correlating the slices.

In order to facilitate manual finding and matching or marking of prominent body structures between images, it is useful to display the images as three-dimensional images on a computer screen and mark the prominent structure on the three-dimensional images, so that the attending doctor will not have to work directly with image slices.

Figure 4A:
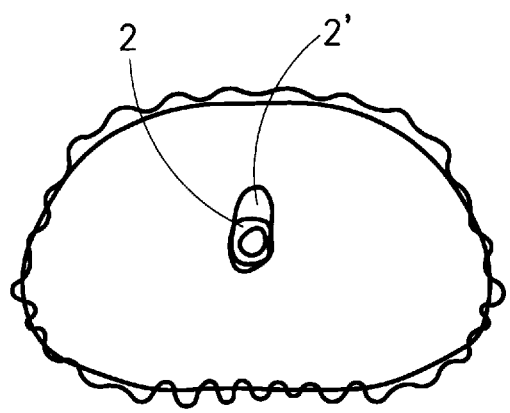
FIG. 4A is a simplified correlated STET image created by aligning and superimposing the STET images from FIG. 2B and FIG. 2C.
Figure 4B:
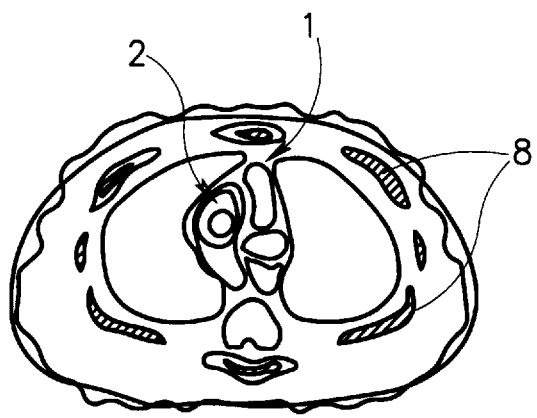
FIG. 4B is a superposition image created from the functional STET image in FIG. 2B and the structural image from FIG. 3.

Once the transformation between the two images is known, many image processing techniques are applicable, for example: image subtraction, rapid flipping of two or more images, superpositioning of outlines of the active areas from one STET image on another STET image or on a CT image and pseudo-coloring of different areas. FIG. 4A shows the superpositioning of the outline of an active area from the STET image 6 on the STET image 6'. FIG. 4B shows the superpositioning of the outline of the active area from the STET image 6 on the CT image 70.

In addition, the present invention enables simultaneous processing and viewing of several images which are registered to each other using the methods described herein. For example, two images are displayed side by side on a computer screen, a portion of one image is marked off and radiation emitted by that portion is computed. The radiation emitted by the matching portion of the other image is calculated and displayed automatically by the computer.

In general, the correlation algorithms used for matching images and slices, between and within modalities and the subsequently derived transformations are any of a variety of methods known in the art of image registration. The following image registration methods are useful in carrying out preferred embodiments of the invention.

1. LANDMARK MATCHING

Corresponding anatomical or external markers are identified in the sets of data to be matched. A minimum root mean square alignment transformation is then calculated to align one set of markers with the other set. Preferably, the markers are identified by an operator.

2. SURFACE MATCHING

The surface representations of two data sets are correlated by finding the transformation which yields the minimum root mean square distance between the two surfaces. This method is described in "Accurate Three-Dimensional Registration of CT, PET and/or MR Images of the Brain", by Pelizzari C. A., et al., Journal of Computer assisted Tomography, volume 13, 1989.

3. VOLUME MATCHING

The two data sets are correlated by finding the transformation which yields the maximum cross correlation value between the sets. This method is described in "MRI-PET Registration with Automated Algorithm", by Woods R. P., et al., Journal of Computer Assisted Tomography, volume 17, 1993.

4. SPATIAL PARAMETERS MATCHING

The two data sets are correlated by matching spatial parameters such as the moments of the data sets. The moments can be matched by finding the principle axis for which they attain their minimal value. This method is described in "The Principle Axes Transformation —A Method for Image Registration", by Alpert, N. M., et al., Journal of Nuclear Medicine, volume 31, 1990.

5. INVARIANT GEODESIC LINES AND POINTS MATCHING

The data sets are analyzed using a differential analysis of their surfaces discrete representation, yielding lines and points which correspond to local maxima and/or minima of surface curvature. A global affine transformation is then found that delivers the best matching of the corresponding lines and points from the two data sets. This method is described in "The External Mesh and the Understanding of 3D Surfaces", research report number 1901 from the Institute National de Recherche en Informative et en Automatic (INRIA), May 1992, and "New Feature Points Based on Geometrical Invariants for 3D Image Registration", research report number 2149 from the INRIA, both by Jean-Phillips Thirion.

Figure 5:
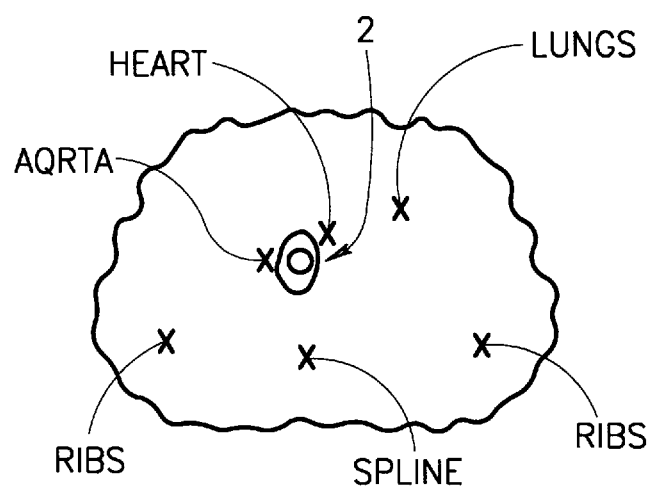
FIG. 5 is a simplified schematic STET image with fiduciary marks for aiding in correlation with structural images such as X-ray CT scans.

In an additional preferred embodiment of the invention, fiduciary marks may be added to the STET image by first adding fiduciary marks to a structural image that is registered to the STET image, and then transforming those marks to the STET image. Additionally, these marks maybe added form a template once the transformation is known. FIG. 5 shows a STET image with fiduciary marks thereon.

In a further preferred embodiment of the invention image, acquisition is gated to body rhythms and motions. Preferably, the structural images are also synchronized in the same manner. For example, gated CT images are used as structural images instead of regular CT images when the STET images are gated. An advantage of combining STET imaging with gating is the ability to correct binned data for patient motion during data acquisition by realignment based on registration of the images. This corrects for smearing otherwise produced by patient motion and enables the use of longer acquisition times. Additionally, data from separate bins is more easily combined.

Figure 6:
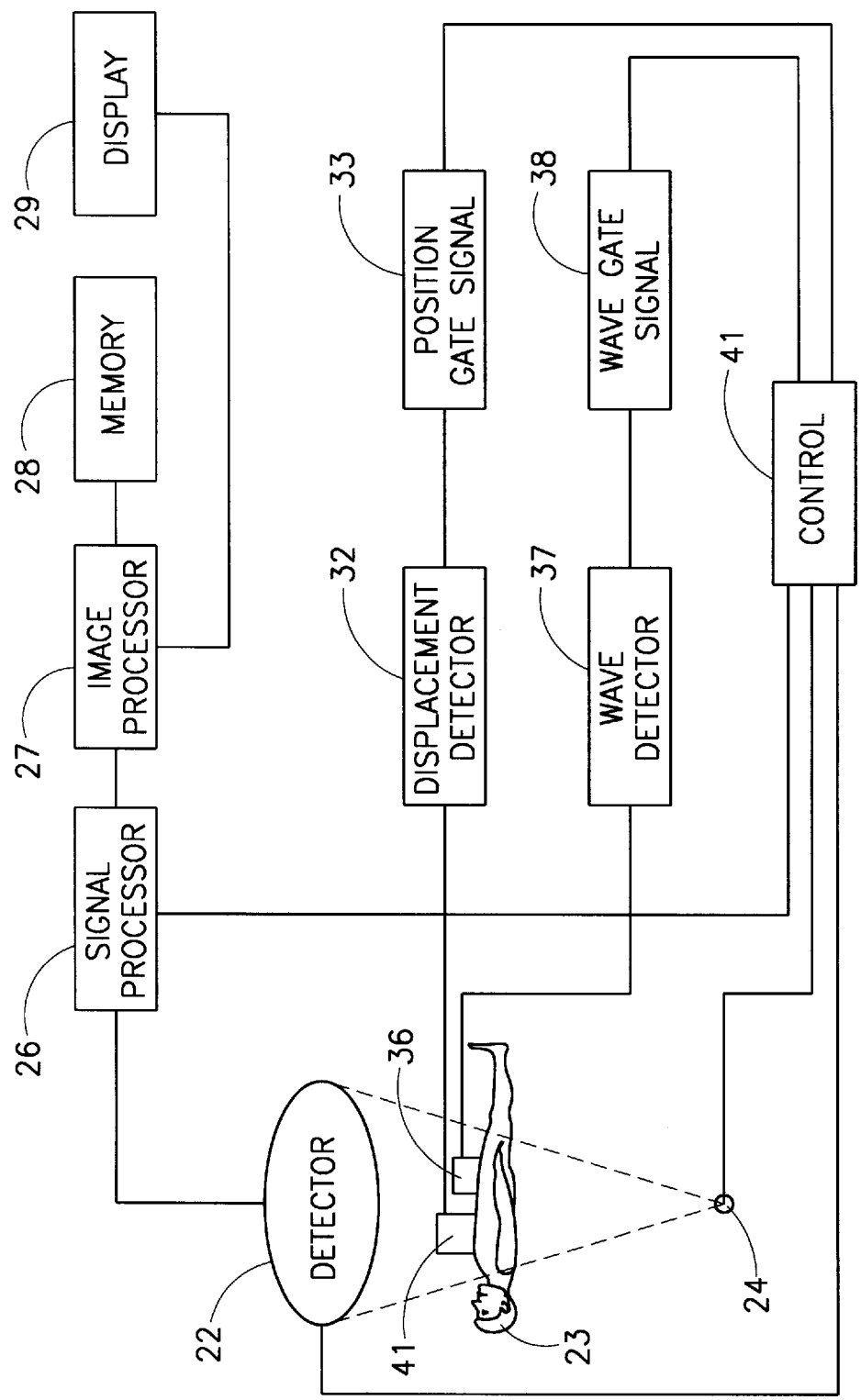
FIG. 6 is a simplified block diagram of a STET system including equipment for cardiac and respiratory gating.

Another advantage is the ability to correct organ motion caused by the gated rhythm, by applying a geometric transformation to data acquired based on the phase of the gated rhythm. Yet another advantage is the ability to register transmission images to emission images even when they are not acquired simultaneously. A transmission image of a patient which is gated to body rhythms can be automatically registered to its corresponding gated emission image, since most of the misalignment between the two images is caused by body rhythms which are in general, repetitive FIG. 6 indicates in simplified block diagram form a STET system 21 equipped to accomplish either cardiac or respiratory gating or both. System 21 generally comprises a detector 22 for detecting radiation. The radiation can be emanating from a patient 23 or from a radiation source 24, typically comprising a radioisotope material. When source 24 is a radioisotope, detector 22 is preferably an Anger type camera.

The output of detector 22 is processed by a signal processor 26. Processor 26 determines the location and energy of photons striking detectors 22.

The output of signal processor 26 is further processed by image processor 27 to provide image data using a memory 28. The processed images are shown on display 29.

Gating controls are provided for system 21. More paticularly, respiratory gating uses a position sensor 31 which senses the thorax position of patient 23 during the STET process. The sensed displacement is operated on to provide windows or bins using a displacement detector 32. A position gate signal unit 33 provides gating signals to signal processor 26 based on the thorax position determined by detector 32. The cardiac gating system senses the heart beat with a sensor 36. The R-wave is detected by a wave detector 37. A cardiac gating signal is provided to signal processor 26 by a wave gate signal unit 38 responsive to detection of the R-wave by detector 37. U.S. Pat. No. 4,617,938, the disclosure of which is incorporated herein by reference, describes a gating system.

STET system 21 is shown to be under the control of a controller 41 which supplies the appropriate control and timing signals.

The present invention was described in the context of nuclear medicine imaging. However, the present invention is applicable to other types of imaging systems, provided that functional images (as described herein) have structural images that are registered to them where needed. Additionally, structural images of modalities other than X-ray CT, MRI, ultrasound and SPECT can be registered to nuclear medicine images by utilizing the present invention.

It will be appreciated by person skilled in the art that the present invention is not limited by what has been particularly shown and described herein. Rather the scope of the present invention is defined only by the claims which follow:

We claim:

1. A method of registering a functional image to a structural diagnostic image comprising:

providing a functional emission nuclear image of a patient as a functional image;

providing a first structural image of said patient;

providing a second structural image, said second structural image comprising a nuclear medicine image and having a known positional relationship to said functional nuclear image;

finding a first mapping transformation between said first and second structural images;

determining a second mapping transformation between said functional image and said first structural image based on said first mapping transformation and said known positional relationship; and gating at least said functional image to at least one of a patient's body rhythms.

2. The method according to claim 1, wherein said body rhythm is the cardiac rhythm.

3. The method according to claim 1, wherein said body rhythm is the respiratory rhythm.

4. The method according to claim 1, wherein said gating comprises binning.

5. The method according to claim 1, further comprising providing a second functional image that has a known positional transformation to said first structural image and binning said functional images in accordance with at least one of said patient's body rhythms.

6. The method according to claim 1, further comprising providing a second functional image, wherein said second functional image has a known positional transformation to said first structural image and wherein said functional images are acquired in different phases of said rhythm.

7. The method according to claim 6, further comprising combining said functional images into a third functional image.

8. The method according to claim 1, wherein said gating comprises windowing.

9. The method according to any one of claims 1-8, wherein said functional image is one of a SPECT (Single Photon Emission Computerized Tomography) and STET (Simultaneous Transmission and Emission Tomography) image.

10. The method according to claim 9, wherein said second structural image is one of a SPECT and STET image.

11. The method according to any one of claim 1–8, wherein said second structural image is one of a SPECT (Single Photon Emissin Computerized Tomography) and STET (Simultaneous Transmission and Emission Tomography) image.

* * * * *